US011345054B2

(12) United States Patent
Li et al.

(10) Patent No.: US 11,345,054 B2
(45) Date of Patent: May 31, 2022

(54) MAGNETIC-INDUCED STIFFNESS CHANGED SOFT ROBOT DRIVE MODULE AND PRODUCTION METHOD THEREOF

(71) Applicant: DALIAN UNIVERSITY OF TECHNOLOGY, Liaoning (CN)

(72) Inventors: Te Li, Liaoning (CN); Yongqing Wang, Liaoning (CN); Haibo Liu, Liaoning (CN); Qile Bo, Liaoning (CN); Boyao Cui, Liaoning (CN); Jianhui Deng, Liaoning (CN); Kuo Liu, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 17/280,716

(22) PCT Filed: Jun. 1, 2020

(86) PCT No.: PCT/CN2020/093736
§ 371 (c)(1),
(2) Date: Mar. 26, 2021

(87) PCT Pub. No.: WO2021/243514
PCT Pub. Date: Dec. 9, 2021

(65) Prior Publication Data
US 2022/0040870 A1 Feb. 10, 2022

(51) Int. Cl.
*B25J 9/10* (2006.01)
*B25J 19/06* (2006.01)
(Continued)

(52) U.S. Cl.
CPC ............... *B25J 19/068* (2013.01); *B25J 9/14* (2013.01); *B25J 15/02* (2013.01); *B25J 9/10* (2013.01); *B25J 19/007* (2013.01)

(58) Field of Classification Search
CPC ....... B25J 9/10; B25J 9/14; B25J 15/02; B25J 19/068
See application file for complete search history.

(56) References Cited

FOREIGN PATENT DOCUMENTS

| CN | 204123396 U | 1/2015 |
|---|---|---|
| CN | 108638046 A | 10/2018 |

(Continued)

*Primary Examiner* — William C Joyce
(74) *Attorney, Agent, or Firm* — Muncy, Geissler, Olds & Lowe, P.C.

(57) ABSTRACT

A magnetic-induced stiffness changed soft robot drive module includes magnetic-induced stiffness changed layer, two-degree-of-freedom pneumatic driver, magnetic core and sealing fixing device. The magnetic-induced stiffness changed layer and two-degree-of-freedom pneumatic driver are printed and formed. The magnetic core can be deformed together with the driver, and a magnetic field can be generated when it is energized. After the magnetic core is installed into the two-degree-of-freedom pneumatic driver, then assembled with the sealing fixing device, a soft robot drive module with one end fixed is finished. The magnetic-induced stiffness changed layer has the fast, reversible and controllable stiffness adjustment ability under the action of electromagnetic field. As its hardness is greater than that of the two-degree-of-freedom pneumatic driver and its position is outside the air cavity, the two-degree-of-freedom pneumatic driver can be restricted from over-expansion and over-extension in the axial direction, making its pneumatic bending deformation controllable.

3 Claims, 3 Drawing Sheets (51) Int. Cl.
*B25J 9/14* (2006.01)
*B25J 15/02* (2006.01)
*B25J 19/00* (2006.01)

(56) References Cited

FOREIGN PATENT DOCUMENTS

| | | |
|---|---|---|
| CN | 108724166 A | 11/2018 |
| CN | 108927791 A | 12/2018 |
| CN | 109571453 A | 4/2019 |
| CN | 110474565 A | 11/2019 |
| WO | WO-2013184192 A2 | 12/2013 |

MAGNETIC-INDUCED STIFFNESS CHANGED SOFT ROBOT DRIVE MODULE AND PRODUCTION METHOD THEREOF

TECHNICAL FIELD

The invention belongs to the technical field of soft robots, and relates to a magnetic-induced stiffness changed soft robot drive module and production method thereof.

BACKGROUND

Soft robot technology is one of the emerging frontiers in the robotics field in recent years. The design of the soft robot is inspired by soft creatures such as elephant trunks, octopus tentacles, and inchworms. Therefore, soft robots no longer use rigid structural joints, but mainly use soft materials such as silicone rubber and hydrogel as their bodies. They have good human-machine-environment interaction and safety. They are used in aerospace, underwater operations, high-end manufacturing, biomedicine and other fields have broad application prospects. However, the current practical application of soft robots has the design problem of "more flexibility but not enough rigidity", which hinders the application process of soft robots. Therefore, in order to make soft robots have both friendly interaction and operational load capacity, soft robots with variable stiffness adjustment capabilities have become a hot research direction.

In 2017, Hongliang Ren of the National University of Singapore and others proposed a method for adjusting the stiffness of the actuator by controlling the positive and negative pressures of the internal cavity of the origami structure in the invention patent application number 201710258747.0. However, the production of the origami structure is more complicated and the drive speed is slow. In 2019, Xufeng Dong of Dalian University of Technology and others proposed a variable stiffness layer made of electrorheological fluid in the invention patent application number 201910853243.2, so as to realize the stiffness adjustment ability of the bending deformation actuator under electronic control, but electrorheological fluid has the problems of poor agglomeration stability and sedimentation stability, and the manufacturing process is not easy.

In summary, fast, controllable, reversible, and integrated variable stiffness capability and flexible motion capability have become the technical goal of the design of the soft robot variable stiffness drive. At present, the overall performance of the variable stiffness drive design still needs to be improved.

SUMMARY

In view of the problems existing in the current technology, the present invention provides a magnetic-induced stiffness changed soft robot drive module and production method thereof. This method uses a magnetic-induced stiffness changed layer made of PDMS and high-purity hydroxyl iron powder as raw materials to achieve rapid, reversible, and controllable stiffness adjustment capabilities under the action of an electromagnetic field; An integrated design configuration of variable stiffness actuators is adopted and a soft robot pneumatic driver that realizes the coexistence of two-degree-of-freedom motion and stiffness adjustment capabilities; the 3D printing process steps of direct ink writing is proposed, and the manufacture of stiffness changed drive module is realized.

In order to achieve the above-mentioned objective, the technical solution adopted by the present invention is as follows:

A magnetic-induced stiffness changed soft robot drive module, including a magnetic-induced stiffness changed layer 1, a two-degree-of-freedom pneumatic driver 2, a magnetic core 3, and a sealing fixing device 4; the magnetic-induced stiffness changed layer 1 and two-degree-of-freedom pneumatic driver 2 are main body of the drive module, they are integrally formed by 3D printing with direct ink writing, and then the magnetic core 3 is packaged in the center, and finally connected with the sealing fixing device 4 to be assembled into the magnetic-induced stiffness changed soft robot drive module.

The magnetic-induced stiffness changed layer 1 is a magnetic control intelligent elastomer composed of magnetizable particles and a silicone rubber matrix, the middle part of which is an arc-shaped structure, the upper and lower ends are fan-shaped structures, and the fan-shaped structure of lower end is provided with an arc-shape opening. The opening is used to pass through a connecting part 204 of the two-degree-of-freedom pneumatic driver 2. The magnetizable particles are submicron hydroxy iron powder, and the rubber matrix is PDMS.

Main body of the two-degree-of-freedom pneumatic drive 2 is a cylindrical structure, and includes four parts: air cavity 201, magnetic-induced stiffness changed layer cavity 202, magnetic core cavity 203, and the connection part 204. The center of the cylindrical structure is provided with a cylindrical cavity along the axial direction. The upper end surface of the cylindrical cavity is open and the lower end surface is closed. The cylindrical cavity serves as a magnetic core cavity 203 for accommodating the magnetic core 3. The upper and lower surfaces of the cylindrical structure are provided with three fan-shaped grooves at equal intervals along the circumferential direction of the cylindrical cavity. The fan-shaped groove is matched with the fan-shaped structure at the upper and lower ends of the magnetic-induced stiffness changed layer 1, and the center angle of the fan-shaped groove on the upper end surface is smaller than the center angle of the fan-shaped groove on the lower end surface. Three through arc-shaped cavities are arranged at equal intervals in the longitudinal direction inside the cylindrical structure. The connection part 204 includes three groups, which are arranged in the three arc-shaped cavities inside the cylindrical structure. Each group includes two plate-shaped structures with a certain arc on the outer side and the inner side, and the length of the connection part 204 is greater than length of two-degree-of-freedom pneumatic drive 2, the upper end of connection part 204 is in contact with the lower surface of the fan-shaped groove on the upper end of the two-degree-of-freedom pneumatic drive 2, and the protruding part of the lower end is inserted into the arc-shaped groove of the sealing fixing device 4. The area between the outer plate-shaped structure and the outer side of the arc-shaped cavity is the magnetic-induced stiffness changed layer cavity 202, which is used to place the magnetic-induced stiffness changed layer 1, and the length of the middle arc structure of the magnetic-induced stiffness changed layer 1 is the same as that of the magnetic-induced stiffness changed layer cavity 202. When printing, the two models are merged and directly integrated into one piece, the area between the two plate-shaped structures is air cavity 201, which is used to accommodate driving gas, and the top of air cavity 201 is closed and the bottom penetrates. The bottom of the connection part 204 can be sealed through the sealing fixing device 4 by matching with the sealing fixing device 4; the inner plate-shaped structure is in contact with the inner surface of the arc-shaped cavity inside the cylindrical structure.

Figure 5:
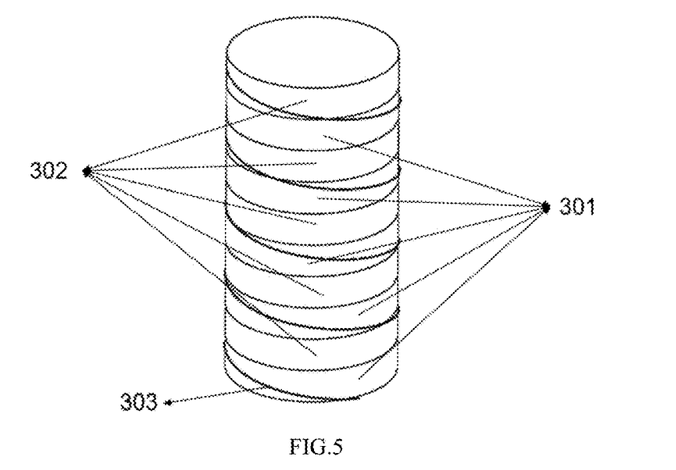
FIG. 5 is a schematic diagram of the structure of the magnetic core.
Figure 6A:
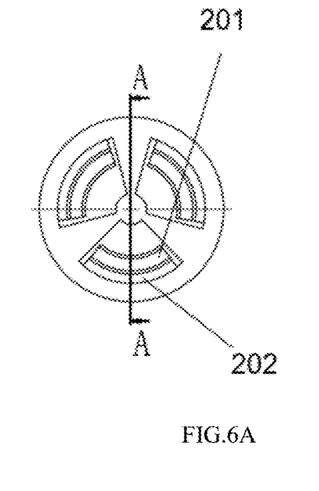
FIGS. 6A and 6B are a top view and a section of the two-degree-of-freedom pneumatic driver.
Figure 6B:
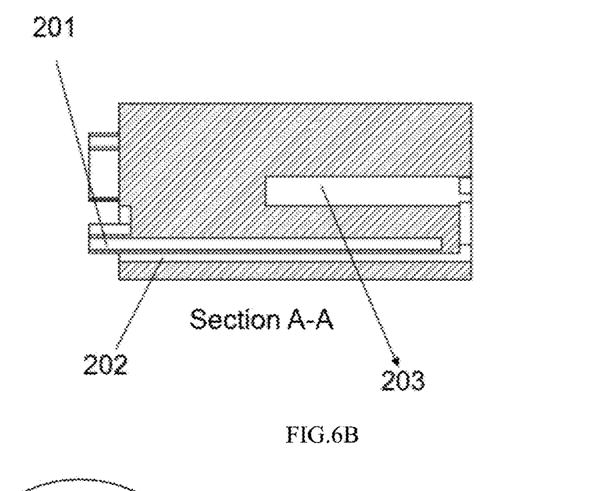
Figure 7:
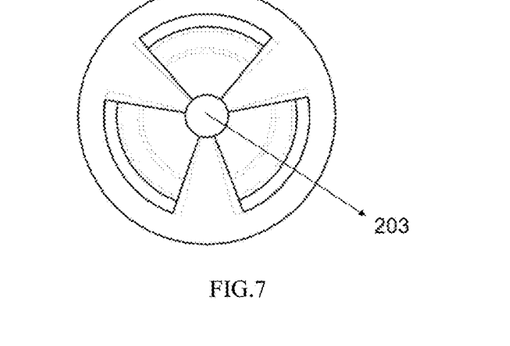
FIG. 7 is a bottom view of the two-degree-of-freedom pneumatic driver.
Figure 8:
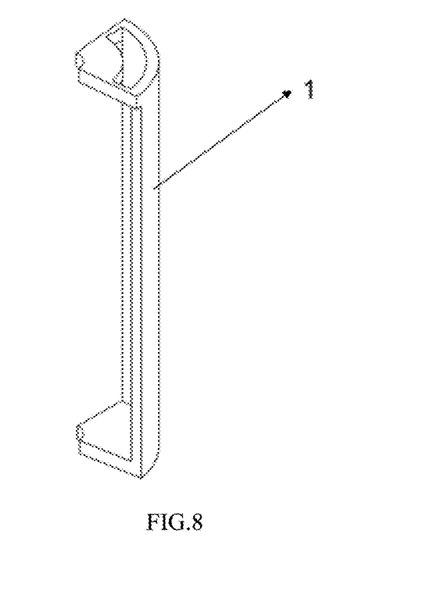
FIG. 8 is a schematic diagram of the structure of the magnetic-induced stiffness changed layer.

The magnetic core 3 is used as a magnetic field generating device which is made by bonding silicon steel sheet 301 and silica gel layer 302 layer by layer. The outer surface of the magnetic core 3 is wrapped with copper conductive coil 303, and it is encapsulated in the magnetic core cavity 203, so integrated with two-degree-of-freedom pneumatic drive 2. Among them, the alternate structure of silicon steel sheet 301 and silica gel layer 302 can ensure that the magnetic core 3 has a certain deformation ability, and will not affect the overall deformation of the driver. A current is applied to the copper conductive coil 303 wound around the outer circumference of the magnetic core 3, and the magnetic core 3 generates a magnetic field. In addition, the magnetic-induced stiffness changed layer 1 and the magnetic core 3 form a closed magnetic circuit; Under the action of a strong magnetic field, the magnetized particles of the magnetic-induced stiffness changed layer 1 can be magnetized, and the interaction energy between the particles is increased, thereby increasing the stiffness of the magnetic-induced stiffness changed layer 1, thereby effectively improving the overall stiffness of the drive module; By adjusting the number of turns and current of the copper conductive coil 303, dynamic stiffness adjustment can be achieved. After the magnetic field is removed, the magnetizable particles are demagnetized, and the interaction energy between the particles is reduced to zero, so that the magnetic-induced stiffness changed layer 1 is demagnetized and restored to its original state. As shown in FIG. 8, when a magnetic field is applied, due to the larger cross-sectional area of the upper and lower ends of the magnetic-induced stiffness changed layer 1, a sector-shaped structure can ensure that the magnetic core 3 and the magnetic-induced stiffness changed layer 1 form a closed-loop magnetic circuit when it is energized.

The sealing fixing device 4 includes an outer flange 401, a middle sealing splint 402, and an inner flange 403. The outer flange 401 is a hollow trapezoidal round table structure, the middle sealing splint 402 and the inner flange 403 are placed in the hollow, and the middle sealing splint 402 is located between the outer flange 401 and the inner flange 403. The convex circumferential structure of the outer flange 401 is provided with three outer flange connecting holes 401-1 at equal distance along the circumferential direction, and the corresponding positions of the middle sealing splint 402 and the inner flange 403 are provided with middle sealing splint connecting hole 402-1 and inner flange connecting hole 403-1. The bolts pass through the outer flange connecting hole 401-1, the middle sealing splint connecting hole 402-1, the inner flange connecting hole 403-1 and the connection part 204 in a horizontal direction in order to be connected, and play a sealing role. The outer ring of the outer flange 401 is also provided with 8 outer flange Mounting holes 401-2 at equal intervals for fixing the ends of the magnetic-induced stiffness changed soft robot drive module. The middle sealing splint 402 is a circular ring structure, and three sets of arc-shaped groove structures are equally spaced on both sides of the circumference. Each group of groove structures includes an inner groove structure close to the inner flange 403 and an outer groove structure close to the outer flange 401. The outer groove structure is used to pass through the two arc-shaped plate structures of connection part 204; each group of groove structures is provided with vent hole 402-2 in the middle (vent hole 402-2 is the vertical direction), which is used to communicate with SP-20 quick connector, and the vent hole 402-2 communicates with the air cavity 201.

A production method of the magnetic-induced stiffness changed soft robot drive module includes the following steps:

Step 1: Prepare the Printing Material for the Magnetic-Induced Stiffness Changed Layer 1

The printing materials of the magnetic-induced stiffness changed layer 1 include PDMS, fumed silica, and high-purity hydroxyl iron powder. The particle size of the high-purity hydroxyl iron powder is less than 10 microns, the purity is greater than or equal to 99% iron content, and the appearance is black ultrafine powder without any impurities. The PDMS is selected from Dow Corning Syglard 184 silicone rubber, which includes basic component A and curing agent B. After the two components are mixed, they can be cured within 48 hours at room temperature.

The preparation process of the material is as follows: First, add basic component A, curing agent B, high-purity hydroxyl iron powder, and fumed silica in a beaker in a mass ratio of 10:1:6:1.25. The addition of fumed silica as a thixotropic agent can make the raw material obtain the mechanical properties required for direct ink writing. Then, put the stirred printing materials into a vacuum box for 5-10 minutes at room temperature to remove air bubbles. Finally, the printing material of the magnetic-induced stiffness changed layer 1 is obtained, which looks like a thicker black colloid.

Step 2: Prepare the Printing Material for the Two-Degree-of-Freedom Pneumatic Drive 2

The printing materials of the two-degree-of-freedom pneumatic drive 2 include PDMS and fumed silica. The PDMS is made of Dow Corning 184 silicone rubber, composed of two components A and B, including basic component A and curing agent B.

The material preparation process is similar to the printing material preparation of the magnetic-induced stiffness changed layer 1: First, add the basic component A, curing agent B, and fumed silica in a beaker at a mass ratio of 10:1:1.25, then stir thoroughly. Among them, the addition of fumed silica as a thixotropic agent can make the raw material obtain the mechanical properties required for direct ink writing. Then, put the stirred printing materials into a vacuum box for 5-10 minutes at room temperature to remove air bubbles. Finally, the printing material of two-degree-of-freedom pneumatic drive 2 is obtained, and the appearance is a relatively viscous off-white colloid.

Step 3: 3D Printing of the Magnetic-Induced Stiffness Changed Layer 1 and Two-Degree-of-Freedom Pneumatic Drive 2

The magnetic-induced stiffness changed layer 1 and two-degree-of-freedom pneumatic drive 2 can be printed and formed continuously from bottom to top, specifically: First, put the printing materials which are made in the Step 1 and Step 2 corresponding to the magnetic-induced stiffness changed layer 1 and the two-degree-of-freedom pneumatic drive 2 into two low-temperature printing heads. Secondly, combine the two models and slice them together then give the two print heads the printing material properties of the magnetic-induced stiffness changed layer 1 and the two-degree-of-freedom pneumatic drive 2 respectively. The air cavity 201 normally leaves space when printing, the magnetic-induced stiffness changed layer 1 corresponding to the position of channel for the magnetic-induced stiffness changed layer 202, directly follows the two-degree-of-freedom pneumatic drive 2 for layer-by-layer printing. When the printing is completed, they are combined into one.

Step 4: Fabrication and Package of Magnetic Core 3

First, five silica gel layers 302 are printed by printing materials of two-degree-of-freedom pneumatic drive 2. After the silica gel layer 302 is cured, it is alternately bonded with 5 silicon steel sheets 301 to make magnetic core 3. Then, the copper conductive coil 303 is wound around the magnetic core 3. Finally, after the magnetic-induced stiffness changed layer 1 and two-degree-of-freedom pneumatic drive 2 are cured in the Step 3, the magnetic core 3 wrapped with the copper conductive coil 303 is put into the magnetic core cavity channel 203. Then, inject liquid heat insulating silica gel into the remaining space of the magnetic core cavity channel 203, and wait for it to be completely solidified to complete the packaging.

Step 5: Assemble the Sealing Fixing Device 4

First, align the inner flange 403 with the center of the inner ring of the connection part 204, and glue and fix it. Secondly, put the middle sealing splint 402 between the connection part 204 and the inner flange 403, and align the middle sealing splint connecting hole 402-1 and the inner flange connecting hole 403-1. Third, put the outer flange 401 on the outer ring of middle sealing splint 402 and connection part 204, and rotate to the outer flange connecting hole 401-1 and middle sealing splint connecting hole 402-1 to align. Finally, use three bolts to connect outer flange 401, middle sealing splint 402, inner flange 403 and connection part 204 through outer flange connecting hole 401-1, middle sealing splint connecting hole 402-1, and inner flange connecting hole 403-1. The side connection gap between the two-degree-of-freedom pneumatic drive 2 and the sealing fixing device 4 is sealed by glass glue to prevent air leakage when large deformation occurs.

Step 6: Perform Pneumatic Control and Magnetic Stiffness Adjustment on the Magnetic-Induced Stiffness Changed Soft Robot Drive Module Connect three SP-20 quick connectors to vent hole 402-2 through threads, and vent hole 402-2 communicates with air cavity 201; Each SP-20 quick connector is externally connected to an air pipe, a proportional valve and an air pump separately, to achieve three-channel high-pressure gas modular pneumatic drive, so that the magnetic-induced stiffness changed soft robot drive module 1 has the ability of individual control and coordinated control.

Further, the hardness of the magnetic-induced stiffness changed layer 1 is higher than the hardness of the two-degree-of-freedom pneumatic drive 2, and the magnetic-induced stiffness changed layer 1 can also limit radial over-expansion and axial expansion of two-degree-of-freedom pneumatic drive 2. The limitation makes the aerodynamic bending deformation of the two-degree-of-freedom pneumatic drive more controllable; At the same time, the magnetic-induced stiffness changed layer 1 is beneficial to increase the load capacity of the drive module of the magnetic-induced stiffness changed soft robot drive module.

The beneficial effect of the present invention is that a magnetic-induced stiffness changed soft robot drive module is designed by adopting the principle of magneto-induced stiffness changed, and a manufacturing process method is proposed. The magnetic-induced stiffness changed soft robot drive module can achieve 2 degrees of freedom bending under the drive of high-pressure gas, and can be used as the basic drive unit of a continuous body robot or a multi-finger dexterous hand; After the copper conductive coil 303 entwined on the magnetic core 3 generated the magnetic field, the driver module relies on magnetic-induced stiffness changed layer 1 to achieve a fast response, controllable and reversible stiffness adjustment ability; The magnetic-induced stiffness changed soft robot drive module is a highly integrated unit module without external device to generate magnetic field, and has a compact and reliable design structure. Its design principle is universal, can be used for variable stiffness soft robots with other motion forms.

In the picture: 1 the magnetic-induced stiffness changed layer; 2 two-degree-of-freedom pneumatic drive; 3 magnetic core; 4 sealing fixing device; 401 outer flange; 402 middle sealing splint; 403 inner flange; 401-2 outer flange Mounting hole; 401-1 outer flange connecting hole; 402-1 middle sealing splint connecting hole; 403-1 inner flange connecting hole; 402-2 vent hole; 201 air cavity; 202 Channel for the magnetic-induced stiffness changed layer; 203 magnetic core cavity channel; 204 connection part; 301 silicon steel sheet; 302 silica gel layer; 303 copper conductive coil.

DETAILED DESCRIPTION

The following describes the embodiments of the present invention in detail with reference to the drawings and technical solutions, but the scope of protection of the present invention is more than the above.

Figure 1:
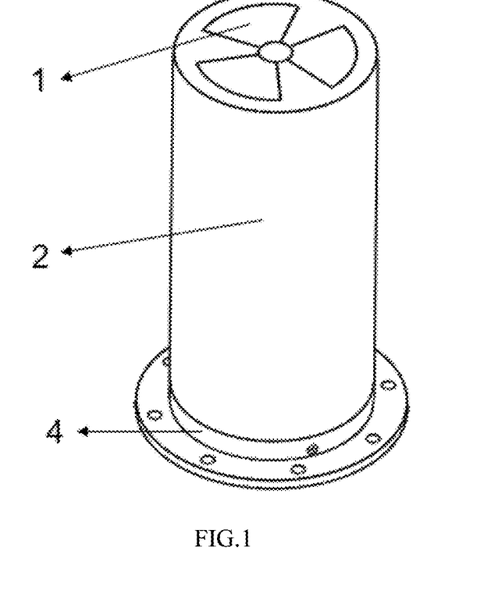
FIG. 1 is a schematic diagram of the overall structure of the magnetic-induced stiffness changed soft robot drive module of the present invention.
Figure 2:
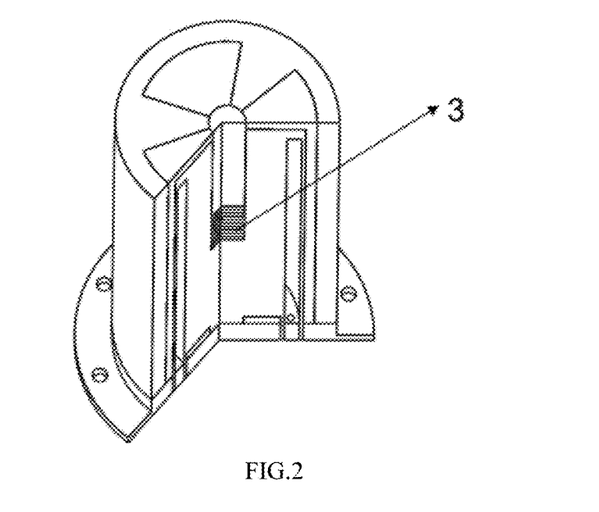
FIG. 2 is a schematic diagram of the internal structure of the magnetic-induced stiffness changed soft robot drive module of the present invention.

The magnetic-induced stiffness changed soft robot drive module of the present invention is composed of the magnetic-induced stiffness changed layer 1, two-degree-of-freedom pneumatic drive 2, magnetic core 3, and sealing fixing device 4. The main body is made by 3D printing with direct ink writing. Among them, the structural design of the magnetic-induced stiffness changed layer 1 and two-degree-of-freedom pneumatic drive 2 satisfy the need for integrated printing and does not require separate production and combination, and has the advantages of compactness, reliability, and simplicity.

The magnetic-induced stiffness changed layer 1 has an arc-shaped column with a length of 112 mm in the middle, and a fan-shaped column with a length of 4 mm at the upper and lower ends respectively, which are embedded in the two-degree-of-freedom pneumatic drive 2. For the lower fan-shaped, there is an arc-shaped opening in the middle of the structure for passing through the connection part 204 of the two-degree-of-freedom pneumatic drive 2. It is a magnetron smart elastomer in which submicron hydroxy iron powder is dispersed into the PDMS matrix. Under the action of the magnetic field generated by the magnetic core 3, the magnetic particles are magnetized, so that the magnetization vector of the particles is aligned with the applied magnetic field, and the interaction energy between the particles is increased, thereby increasing its rigidity. After the magnetic field disappears, the magnetizable particles are demagnetized, the interaction energy between particles is reduced to zero, and the initial state can be restored; the presence of high-purity hydroxyl iron powder also makes the magnetic-induced stiffness changed layer 1 increase its hardness, thereby limiting the effect of excessive radial and axial deformation of the drive. As shown in FIG. 8, when a magnetic field is applied, the upper and lower ends of the magnetic-induced stiffness changed layer 1 have a fan-shaped structure with a larger surface area, which can ensure that the magnetic core 3 can form a closed-loop magnetic circuit that along the axis of the magnetic core, along the fan shape, along the longitudinal direction of the arc-shaped cylinder, and along the horizontal direction of the sector.

The two-degree-of-freedom pneumatic drive 2 is the main part of the magnetic-induced stiffness changed soft robot drive module. The shape is approximately a cylindrical structure with a diameter of 60 mm, including air cavity 201 and channel for the magnetic-induced stiffness changed layer 202, magnetic core cavity channel 203, connection part 204. The cylindrical structure is provided with three arc-shaped cavity structures at equal intervals (120°) along the longitudinal direction, and there are also three sector-shaped groove structures arranged at equal intervals along the horizontal at the upper and lower ends. It is the channel for the magnetic-induced stiffness changed layer 202 used to accommodate the magnetic-induced stiffness changed layer 1; the connection part 204 is a three-group plate structure set in three arc-shaped cavities inside the cylindrical structure, and the length of the connection part 204 is 20 mm longer than the two-degree-of-freedom pneumatic drive. The upper end of connection part 204 is in contact with the lower surface of the fan-shaped groove on the upper end of the two-degree-of-freedom pneumatic drive 2, and the lower end of the protrusion is inserted into the arc of the sealing fixing device 4. The area between the outer plate-shaped structure and the outer side of the arc-shaped cavity is the channel for the magnetic-induced stiffness changed layer 202, which is used to place the magnetic-induced stiffness changed layer 1. When printing, the two models are merged and formed directly into one piece. The area between the set of two plate-shaped structures is air cavity 201, which is used to accommodate driving gas, and the air cavity 201 is closed at the top and penetrated at the bottom, with a length of 110 mm, and the bottom of the connection part 204 passes through and sealing fixing device 4. The position for penetration can be sealed by matching; The inner plate-shaped structure is in contact with the inner surface of the arc-shaped cavity inside the cylinder. The magnetic core cavity 203 is a cylindrical cavity with a depth of 70 mm, it penetrated at the bottom and located at the axis of the two-degree-of-freedom pneumatic drive 2, which is used to accommodate the magnetic core 3 and is subsequently filled with heat-insulating silica gel.

Figure 3:
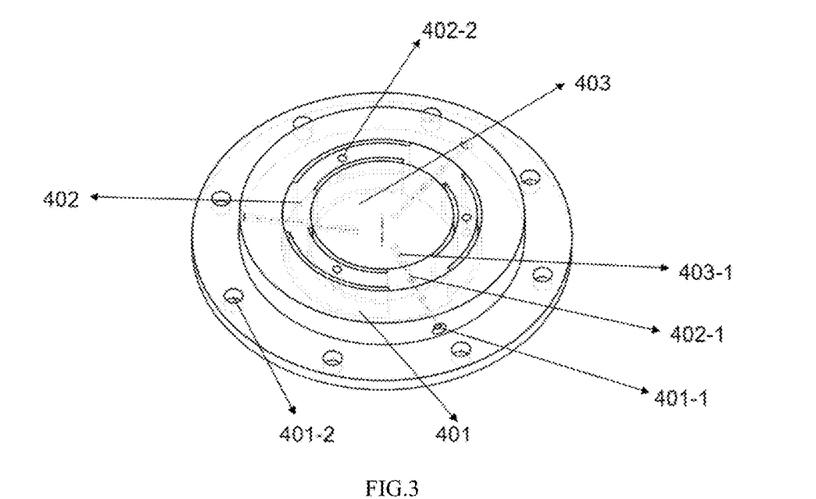
FIG. 3 is a schematic diagram of the structure of the sealing fixing device.
Figure 4:
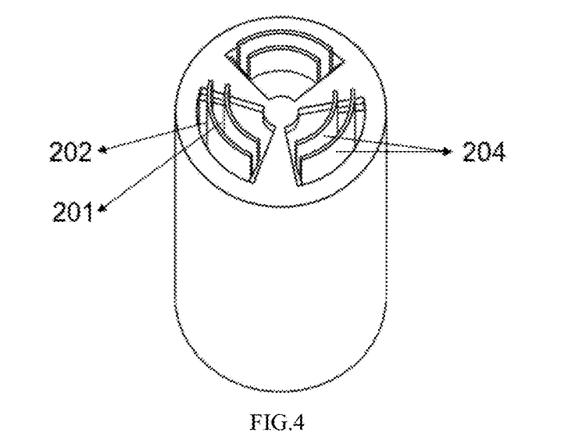
FIG. 4 is a schematic diagram of the structure of the two-degree-of-freedom pneumatic driver.

As shown in FIG. 5, the magnetic core 3 is composed of a silicon steel sheet 301 and a silica gel layer 302 laminated on each other. The copper conductive coil 303 wound around the magnetic core 3 and it can be energized to apply a magnetic field;

The sealing fixing device 4 is composed of an outer flange 401, a middle sealing splint 402, and an inner flange 403. The hollow of the outer flange 401 is used to accommodate the middle sealing splint 402 and the inner flange 403. The middle sealing splint 402 is located on the outer ring of the inner flange 403. The convex circumferential structure of the outer flange 401 is provided with three outer flange connecting holes 401-1 at equal intervals along the circumferential direction. The corresponding positions of the middle sealing splint 402 and the inner flange 403 are also provided with middle sealing splint connecting hole 402-1, inner flange connecting hole 403-1. The bolts pass through outer flange connecting hole 401-1, middle sealing splint connecting hole 402-1, inner flange connecting hole 403-1 and connection part 204 in order in the horizontal direction, so to achieve the sealing effect. The outer ring of the outer flange 401 is also provided with 8 outer flange mounting holes 401-2 at equal intervals for fixing the ends of the magnetic-induced stiffness changed soft robot drive module. The middle sealing splint 402 has three groups of arc-shaped groove structures at equal intervals on both sides of the circumference, and each group of groove structures includes an inner groove structure close to the inner flange 403 and an outer groove structure close to the outer flange 401 structure, and the arc length of the inner groove structure is smaller than that of the outer groove structure. There is a vent hole 402-2 in the middle of each group of groove structure (vent hole 402-2 is the vertical direction), which is used to connect with SP-20 quick connectors, and the vent hole 402-2 communicates with the air cavity 201. Among them, the convex circumferential structure of the outer flange 401 has the same diameter as the two-degree-of-freedom pneumatic drive 2.

A manufacturing method of the magnetic-induced stiffness changed soft robot drive module is specifically as follows:

Step 1: Prepare the Printing Material for the Magnetic-Induced Stiffness Changed Layer 1

The magnetic-induced stiffness changed layer 1 is a magnetron intelligent elastomer in which sub-micron hydroxy iron powder is dispersed into the PDMS matrix. The printing material is mainly composed of PDMS, fumed silica and high-purity hydroxy iron powder that are used to change its performance. The particle size of the high-purity hydroxy iron powder is less than 10 microns, the purity is greater than or equal to 99% iron content, and the appearance is black ultrafine powder without any impurities. The PDMS is selected from the United States Dow Corning Syglard 184 silicone rubber, composed of two components A and B, including basic component A and curing agent B. After the two components are mixed, they can be cured within 48 hours at room temperature. The preparation process of the material is as follows: First, add the basic component A, curing agent B, high-purity hydroxyl iron powder, and fumed silica in a beaker with a mass ratio of 10:1:6:1.25, then stir fully. Among them, the addition of fumed silica as a thixotropic agent can make the raw material obtain the mechanical properties required for direct ink writing. The fumed silica is sieved with a metal mesh before adding to the break in order to prevent the agglomerated fumed silica from clogging the printing needle; Second, the stirred printing materials are put into a vacuum box for 5-10 minutes at room temperature to remove bubbles. Make sure that no bubbles are visible to the naked eye in the printing material. At this point, the printing material of the magnetic-induced stiffness changed layer 1 is prepared, and the appearance is a thicker black colloid.

Step 2: Prepare the Printing Material for the Two-Degree-of-Freedom Pneumatic Drive 2

The printing material of the two-degree-of-freedom pneumatic drive 2 is composed of PDMS and fumed silica. The PDMS is selected from Dow Corning 184 silicone rubber, which is composed of two components A and B, including basic component A and curing agent B. The material preparation process is similar to the material preparation of the magnetic-induced stiffness changed layer 1: First, the basic component A, curing agent B, and fumed silica are added in a beaker with a mass ratio of 10:1:1.25 and fully stirred. Among them, the addition of fumed silica as a thixotropic agent can make the raw materials obtain the mechanical properties required for direct ink writing. Then, the stirred printing raw materials are put into a vacuum box for 5-10 minutes at room temperature to remove bubbles. At this point, the material configuration is completed, and the appearance is a relatively viscous off-white colloid.

Step 3: 3D Printing of the Magnetic-Induced Stiffness Changed Layer 1 and Two-Degree-of-Freedom Pneumatic Drive 2

First, combine the magnetic-induced stiffness changed layer 1 and two-degree-of-freedom pneumatic drive 2 model to slice in the slicing software of the printer. Secondly, the two prepared materials are placed in two low-temperature print heads and the two print heads are assigned their material properties in the control software. Finally, modify the speed, pressure and other parameters according to the trial printing situation, and then start printing. The material of the two-degree-of-freedom pneumatic drive 2 has high consumption, and the material of one cylinder is not enough to complete the printing. So it is necessary to prepare materials during the printing. The magnetic-induced stiffness changed soft robot drive module includes the main structure: the magnetic-induced stiffness changed layer 1 and the two-degree-of-freedom pneumatic drive 2, they can be combined into one body and printed continuously from bottom to top. The air cavity 201 normally leaves space when printing, and the magnetic-induced stiffness changed layer 1 corresponding to the position of channel for the magnetic-induced stiffness changed layer 202 is printed layer by layer directly following the two-degree-of-freedom pneumatic drive 2. After the printing is completed, the two are combined into one, without cumbersome steps such as bonding and combining.

Step 4: Fabrication and Package of Magnetic Core 3

First, use material of the two-degree-of-freedom pneumatic drive 2 to print 5 silica gel layers 302. After curing, it is alternately bonded with 5 silicon steel sheets 301 to make a magnetic core 3, and a copper conductive coil 303 is wrapped around it. After the magnetic-induced stiffness changed layer 1 and the two-degree-of-freedom pneumatic drive 2 are cured, put the manufactured magnetic core 3 into the magnetic core cavity channel 203, and then inject the liquid insulating silica gel into the remaining space of the magnetic core cavity channel 203, and wait for it to be completely cured before the package. The laminated structure of the silicon steel sheet 301 and silica gel layer 302 contained in the magnetic core 3 is to prevent the purely silicon steel sheet material from being too hard and hindering the deformation of the two-degree-of-freedom pneumatic drive 2. Since the magnetic core generates heat when it is energized, it may melt the silicone rubber material of the drive, so insulating silicone is adopted.

Step 5: Assemble the Sealing Fixing Device 4

The sealing fixing device 4 includes an outer flange 401, a middle sealing splint 402, and an inner flange 403, as shown in FIG. 3. The outer ring diameter of the inner flange 403 is 30 mm, which is the same as the inner diameter of the connection part 204. The outer flange 401 has an outer ring diameter of 60 mm, an inner ring diameter of 42 mm, and a base diameter of 80 mm. The outer flange Mounting hole 401-2 can be used to fix one end of the magnetic-induced stiffness changed soft robot drive module. The specific assembly process is as follows: First, align the inner flange 403 with the center of the connection part 204 then glue and fixed it. Secondly, put the middle sealing splint 402 between the connection part 204 and the inner flange 403, and align the middle sealing splint connecting hole 402-1 and the inner flange connecting hole 403-1. Third, put the outer flange 401 on the outer ring of the middle sealing splint 402 and rotate it to the outer flange connecting hole 401-1 and the middle sealing splint connecting hole 402-1 to align. Finally, use three bolts to connect outer flange 401, middle sealing splint 402, inner flange 403 and connection part 204 through outer flange connecting hole 401-1, middle sealing splint connecting hole 402-1, and inner flange connecting hole 403-1.

Furthermore, on the cylindrical side of the two-degree-of-freedom pneumatic drive 2, the joint with the sealing fixing device 4 is coated with glass glue to seal it to prevent air leakage during large deformation.

Step 6: Perform Pneumatic Control and Magnetic Stiffness Adjustment on the Magnetic-Induced Stiffness Changed Soft Robot Drive Module Connect three SP-20 quick connectors to the vent hole 402-2 through threads. The vent hole 402-2 ensures that the input driving gas can enter the air cavity 201. Each SP-20 quick connector is externally connected to the air pipe, proportional valve and air pump separately, so as to realize the three-channel high-pressure gas pneumatic modularization drive, so that the magnetic-induced stiffness changed soft robot drive module has the ability of independent control and coordinated control. Ventilate three air cavity 201 at the same time, the magnetic-induced stiffness changed soft robot drive module will elongate axially. After applying air pressure to one or two of the air cavity 201, the ventilation of air cavity 201 with the non-ventilated air cavity corresponding to the part of the magnetic-induced stiffness changed soft robot drive module will produce asymmetrical elongation, so the whole body will be bent. Among them, the hardness of the magnetic-induced stiffness changed layer 1 is higher than the hardness of the two-degree-of-freedom pneumatic drive 2, which limits the radial and axial over expansion generated by the two-degree-of-freedom pneumatic drive 2 and increase its the output load capacity.

By energizing the magnetic core 3 to apply a magnetic field, the magnetic-induced stiffness changed layer 1 will be magnetized to increase the stiffness. After testing, under normal conditions, it is found that the zero field modulus of the magnetic-induced stiffness changed layer 1 is 320 Kpa, under the excitation of 100 mT magnetic field, its elastic modulus is 450 KPa; Under the excitation of 200 mT magnetic field, its elastic modulus is 650 KPa; Under the excitation of a 300 mT magnetic field, its elastic modulus is 800 KPa. It can be seen that the magnetic-induced stiffness changed layer 1 can effectively increase its stiffness under magnetic field excitation, and the increase in stiffness can be controlled by the strength of the magnetic field, so that real-time stiffness of the magneto-induced stiffness changed soft robot drive module can be realized in the process of movement.

The above-mentioned examples only express the implementation of the present invention, but cannot therefore be understood as a limitation on the scope of the patent of the present invention. It should be pointed out that for technicians in the related field, without departing from the concept of the present invention, several modifications and improvements can also be made, all of which belong to the protection scope of the present invention.

The invention claimed is:

1. A magnetic-induced stiffness changed soft robot drive module, including magnetic-induced stiffness changed layer, two-degree-of-freedom pneumatic drive, magnetic core, sealing fixing device; the magnetic-induced stiffness changed layer, two-degree-of-freedom pneumatic drive are main body of the drive module, the magnetic core is encapsulated in the center after integral forming of the magnetic-induced stiffness changed layer, two-degree-of-freedom pneumatic drive, and finally connected to the fixing device so as to assemble into the magnetic-induced stiffness changed soft robot drive module;

the magnetic-induced stiffness changed layer is a magnetron smart elastomer composed of magnetizable particles and a silicon rubber matrix; middle part of the magnetron smart elastomer is an arc-shaped structure, and upper and lower ends are fan-shaped structures;

among them, there is an arc-shaped opening in middle of the lower fan-shaped structure for passing through connection part of the two-degree-of-freedom pneumatic drive;

main body of the two-degree-of-freedom pneumatic drive is cylindrical structure, including four parts: air cavity, channel for the magnetic-induced stiffness changed layer, magnetic core cavity, the connection part; center of the cylindrical structure is provided with a cylindrical cavity along axial direction, the upper end of the cylindrical cavity is open and the lower end is closed, the cylindrical cavity serves as a magnetic core cavity channel for accommodating the magnetic core; upper and lower surfaces of the cylindrical structure are provided with three fan-shaped grooves at equal intervals along circumferential direction of the cylindrical cavity, and the fan-shaped grooves are matched with the fan-shaped structures at the upper and lower ends of the magnetic-induced stiffness changed layer; interior of the cylindrical structure is provided with three arc-shaped cavities at equal intervals along longitudinal direction; the connection part includes three groups, which are set in the three arc-shaped cavities, and each group includes two curved plate-shaped structures, area between one plate-shaped structure and the outer side of the arc-shaped cavity is the channel for the magnetic-induced stiffness changed layer, which is used to place the magnetic-induced stiffness changed layer, and the other plate-shaped structure is in contact with the inner surface of the arc-shaped cavity inside the cylindrical structure, area between the two plate-shaped structures is the air cavity for accommodating driving gas, and the air cavity is closed at top and penetrates through bottom; the length of the connection part is greater than the length of the two-degree-of-freedom pneumatic drive, upper end of the connection part is in contact with lower surface of the fan-shaped groove on upper end surface of the two-degree-of-freedom pneumatic drive, protruding part of lower end is inserted into the arc-shaped groove of the sealing fixing device;

the magnetic core is used as a magnetic field generator, which is made of silicon steel sheet and silica gel layer by bonding and lamination, and the outer surface of the magnetic core is wrapped with a copper conductive coil; the magnetic core wrapped with the copper conductive coil is encapsulated in the magnetic core cavity and integrated with the two-degree-of-freedom pneumatic drive; by adjusting number of turns and current of the copper conductive coil, the stiffness of the drive module is adjusted;

the sealing fixing device includes an outer flange, a middle sealing splint, and an inner flange; the outer flange is a hollow trapezoidal round table structure, the middle sealing splint and the inner flange are placed in the hollow, convex structure of the outer flange is provided with connecting holes, corresponding positions of the middle sealing splint and inner flange are provided with connecting holes; the bolts pass through the connecting holes along horizontal direction and make a matching connection with the connection part, which plays a sealing role; the outer flange has mounting holes on outer ring for fixing the end of the magnetic-induced stiffness changed soft robot drive module; the middle sealing splint is a ring structure, two sides of circumference of the ring structure has three arc-shaped groove structures at equal intervals, which are used to insert the arc-shaped plate-shaped structure of the connection part; the ring structure is also provided with a vent hole that communicates with the air cavity, which is connected with a quick connector.

2. The magnetic-induced stiffness changed soft robot drive module according to claim 1, wherein the magnetizable particles are submicron hydroxy iron powder, and the rubber matrix is polydimethylsiloxane (PDMS).

3. A production method of the magnetic-induced stiffness changed soft robot drive module according to claim 1, comprising steps of:

step 1: preparing printing material for the magnetic-induced stiffness changed layer; the printing material of the magnetic-induced stiffness changed layer includes silicone rubber, fumed silica, and high-purity hydroxyl iron powder; the silicone rubber includes basic components and curing agents; mixing basic component A, curing agent B, high-purity hydroxy iron powder, and fumed silica in a mass ratio of 10:1:6:1.25, and putting them into a vacuum box to remove bubbles, then obtaining the printing material of the magnetic-induced stiffness changed layer;

step 2: preparing printing material for the two-degree-of-freedom pneumatic drive; the printing material of the two-degree-of-freedom pneumatic drive includes silicone rubber and fumed silica; the silicone rubber includes basic components and curing agents; mixing basic component A, curing agent B, and fumed silica in a mass ratio of 10:1:1.25, and putting them into a vacuum box to remove bubbles, then obtaining the printing material of the two-degree-of-freedom pneumatic drive;

step 3: 3D printing of the magnetic-induced stiffness changed layer and two-degree-of-freedom pneumatic drive; firstly, loading the printing materials of the magnetic-induced stiffness changed layer and the two-degree-of-freedom pneumatic drive into two low-temperature print heads; secondly, combining two model to slice, then giving two print heads the printing material properties of the magnetic-induced stiffness changed layer and the two-degree-of-freedom pneumatic drive; leaving space for the air cavity normally when printing, and printing the magnetic-induced stiffness changed layer corresponding to the position of channel for the magnetic-induced stiffness changed layer layer by layer directly following the two-degree-of-freedom pneumatic drive; after the printing is completed, the magnetic-induced stiffness changed layer and the two-degree-of-freedom pneumatic drive are naturally combined into a whole;

step 4: fabrication and package of magnetic core; firstly, using the printing material of the two-degree-of-freedom pneumatic drive to print 5 silica gel layers; after curing, bonding 5 silica gel layers alternately with 5 silicon steel sheet to make a magnetic core; then wrapping the copper conductive coil around the magnetic core; finally, after the magnetic-induced stiffness changed layer and the two-degree-of-freedom pneumatic drive are cured, putting the magnetic core wrapped with the copper conductive coil into the magnetic core cavity channel, and then injecting liquid insulating silica gel into remaining space of the magnetic core cavity channel, waiting for the liquid insulating silica gel to be completely cured before the package;

step 5: assembling the sealing fixing device; firstly, aligning the inner flange with center of the inner ring of the connection part, then gluing and fixing the inner flange; secondly, putting the middle sealing splint between the connection part and the inner flange, and aligning middle sealing splint connecting hole and inner flange connecting hole; third, putting the outer flange on outer ring of middle sealing splint and connection part and rotating to the outer flange connecting hole and middle sealing splint connecting hole to align; finally, using bolts to connect outer flange, middle sealing splint, inner flange and connection part; sealing the side connection gap between the two-degree-of-freedom pneumatic drive and the sealing fixing device by glass glue;

step 6: performing pneumatic control and magnetic stiffness adjustment on the magnetic-induced stiffness changed soft robot drive module; connecting three quick connectors to vent hole through threads; each quick connector is externally connected to an air pipe, a proportional valve and an air pump separately, to achieve three-channel high-pressure gas modular pneumatic drive.

* * * * *